(12) United States Patent
Ueyama (10) Patent No.: US 6,603,401 B1
(45) Date of Patent: Aug. 5, 2003

(54) ELECTRONIC LOCK CONTROL SYSTEM AND HOME MEDICAL MANAGEMENT SYSTEM

(75) Inventor: Kenji Ueyama, Hirakata (JP)

(73) Assignee: Sanyo Electric Co., Ltd., Moriguchi (JP)

( * ) Notice: Subject to any disclaimer, the term of this patent is extended or adjusted under 35 U.S.C. 154(b) by 15 days.

(21) Appl. No.: 10/030,071

(22) PCT Filed: Jul. 7, 2000

(86) PCT No.: PCT/JP00/04577

§ 371 (c)(1),
(2), (4) Date: Jan. 10, 2002

(87) PCT Pub. No.: WO01/04441

PCT Pub. Date: Jan. 18, 2001

(30) Foreign Application Priority Data

Jul. 12, 1999 (JP) ............................................. 11-198050

(51) Int. Cl.[7] ............................................... G08B 23/00
(52) U.S. Cl. .............................. 340/573.1; 340/286.07; 340/540; 340/573.4
(58) Field of Search .......................... 340/573.1, 573.4, 340/573.7, 286.06, 280.07, 539, 540, 545.1, 506, 825.06, 825.32, 825.49, 542; 70/144, 298.3, 274; 128/886, 900, 904

(56) References Cited

U.S. PATENT DOCUMENTS 3,967,478 A * 7/1976 Guinn ..................... 340/573.1
5,751,214 A * 5/1998 Cowley et al. .......... 340/573.1
6,348,867 B1 * 2/2002 Myllymaki .............. 340/573.1

* cited by examiner

Primary Examiner—Anh La
(74) Attorney, Agent, or Firm—Armstrong, Westerman & Hattori, LLP (57) ABSTRACT

The invention provides a home medical management system comprising a portable unit (1) to be worn on the body of the user for measuring a physiological quantity, and a home unit (4) installed at a home of the user and adapted to wirelessly communicate with the portable unit (1) for judging the physical condition of the user according to the physiological quantity measured by the portable unit (1) and notifying an emergency center (32) of occurrence of an emergency in the event of the emergency occurring. The home unit (2) transmits an unfastening command to an electronic lock (41) fastening the front door of the user's home in the event of an emergency occurring, whereby the lock (41) is unfastened, permitting ambulance attendants to enter the room where the user is present.

9 Claims, 7 Drawing Sheets

ELECTRONIC LOCK CONTROL SYSTEM AND HOME MEDICAL MANAGEMENT SYSTEM

TECHNICAL FIELD

The present invention relates to electronic lock control systems for controlling fastening and unfastening of a lock attached to a door, and home medical management systems comprising the electronic lock control system.

BACKGROUND ART

With the advent of the aging society, so-called home medical management systems are proposed and placed into actual use. In the case of such a system, users who are chiefly bedridden sick persons and elderly people wear various sensors for.measuring physiological quantitys such as body temperature and blood pressure. The physiological quantity data obtained by the sensors is sent from time to time or periodically from an information terminal unit (hereinafter referred to as the "home unit") installed at the user's home to a center unit installed at a hospital or like medical institution (hereinafter referred to as the "center") via a telephone line. The center unit receives the quantity data sent from the home unit and conducts the management of the data. Further by checking the data, the doctor can provide instructions on medical care, medication or other necessary procedure.

Such home medical management systems generally support the function of reporting an emergency occurring in the user. This emergency report is automatically made by pushing a button on a pendant wireless transmitter carried by the user, or upon the home unit detecting an output, in excess of a hazardous level, of the physiological quantity sensor worn by the user. In response to the emergency report, the center makes arrangements to send an ambulance or the like to the user's home whose address has already been registered.

However, even if the ambulance arrives at the user's home following the emergency report, the attendants of the ambulance are unable to enter the interior of the user's home if the front door is locked up. Even if they are able to enter the house, it would become too late because the rescue takes much time.

An object of the present invention, which has been accomplished in view of the above problem, is to provide an electronic lock control system which is adapted to rescue the user promptly in response to an emergency report, and a home medical management system.

DISCLOSURE OF THE INVENTION

The present invention provides an electronic lock control system for controlling fastening and unfastening of an electronic lock attached to a door. The system is characterized in that the system comprises means for transmitting an unfastening command to the electronic lock in operative relation with communication with a predetermined destination. When a hospital or the family is notified of an emergency by the system thus constructed, the electronic lock attached, for example, to the front door of the user's home is unfastened in operative relation with the notification.

The electronic lock control system of the invention is characterized in that the system comprises means to be worn on the body of the user for measuring a physiological quantity, and means for conducting communication with a predetermined destination and transmitting an unfastening command to the electronic lock, in accordance with the result of measurement by the physiological quantity measuring means. When the result obtained by the measuring means reveals a hazardous value, the hospital, family or like destination is automatically notified of the emergency, and the electronic lock on the front door or like door of the user's home is unfastened.

The electronic.lock control system of the invention further comprises means for notifying the user that the unfastening command has been transmitted from the transmitting means to the electronic lock. The system thus constructed enables the user to recognize that the electronic lock of his home is unfastened.

The electronic lock control system of the invention further comprises means for canceling the notification by the notifying means, and the transmitting means transmits the unfastening command to the electronic lock in operative relation with the cancellation of the notification by the canceling means. The system thus constructed enables the user to cancel the notification by the notifying means even if the electronic lock on the door is unfastened in operative relation with the emergency notification, whereby the electronic lock can be automatically fastened.

As described above, the electronic lock control system according to the present invention is adapted to unfasten the electronic lock on the front door in operative relation with an emergency communication, so that the person receiving the emergency communication can enter the room where the user is present through the unlocked front door, consequently making it possible to rescue and transport the user promptly.

The present invention provides a home medical management system comprising a portable unit 1 to be worn on the body of the user for measuring a physiological quantity, and a home unit 4 installed at a home of the user and adapted to wirelessly communicate with the portable unit 1 for judging the physical condition of the user according to the physiological quantity measured by the portable unit 1 and notifying a predetermined destination of occurrence of an emergency in the event of the emergency occurring, the system being characterized in that the home unit 2 is provided with means for transmitting an unfastening command to an electronic lock fastening a door of the user's home in the event of an emergency occurring.

When a hospital, family or other destination is notified of the occurrence of an emergency by the home medical management system of the present invention, the electronic lock attached, for example, to the front door of the user's home is automatically unfastened, so that the person receiving the notification can open the door of the home of the user developing the emergency to enter the room and rescue and transport the user promptly.

The present invention further provides a home medical management system comprising a portable unit 1 to be worn on the body of the user for measuring a physiological quantity, and a home unit 4 installed at a home of the user and adapted to wirelessly communicate with the portable unit 1 for judging the physical condition of the user according to the physiological quantity measured by the portable unit 1 and notifying a predetermined destination of occurrence of an emergency in the event of the emergency occurring, the system being characterized in that the home unit 2 is provided with means for transmitting to the destination a password for unfastening an electronic lock fastening a door of the user's home in the event of an emergency occurring. The destination to be notified of the occurrence of emergency can be an emergency center 32 for dispatching ambulance attendants.

With the home medical management system of the present invention, the password for opening the electronic lock of the user's home is sent to the emergency center 32 for the ambulance attendant to unfasten the lock using the password. Accordingly, the front door is held locked until the ambulance attendants arrive at the user's home. This assures the user's home of security.

The present invention further provides a home medical management system comprising a portable unit 1 to be worn on the body of the user for measuring a physiological quantity, a home unit 4 installed at a home of each of users and adapted to wirelessly communicate with the portable unit 1 for judging the physical condition of the user according to the physiological quantity measured by the portable unit 1 and notifying an emergency center 32 for dispatching ambulance attendants of occurrence of an emergency in the event of the emergency occurring, and a center unit 31 connected to the home units 2 of the users for communication therewith and having registered therein a password for unfastening an electronic lock fastening a door of the home of each user. The home unit 2 has means for notifying the center unit 31 of occurrence of an emergency. The center unit 31 comprises means having stored therein the password for unlocking the door of each user's home, means for extracting the password for unlocking the door of the home of the user developing an emergency in response to the notification of occurrence of the emergency from his home unit 2, and means for outputting the extracted password.

Incidentally, the outputting means of the center unit 31 is installed at a location where the attendant of the emergency center 32 can receive the output thereof.

With the home medical management system of the present invention, the center unit has stored therein in advance the password for unfastening the electronic lock of each user's home, such that the ambulance attendant unfastens the electronic lock of the user's home with the password as extracted in accordance with an emergency notification. Accordingly, the electronic lock is held fastened until the ambulance attendants arrive at the user's home. This assures the user's home of security.

BEST MODE OF CARRYING OUT THE INVENTION

With reference to the drawings, a description will be given of embodiments of home medical management system of the invention.

Construction of the System

Figure 1:
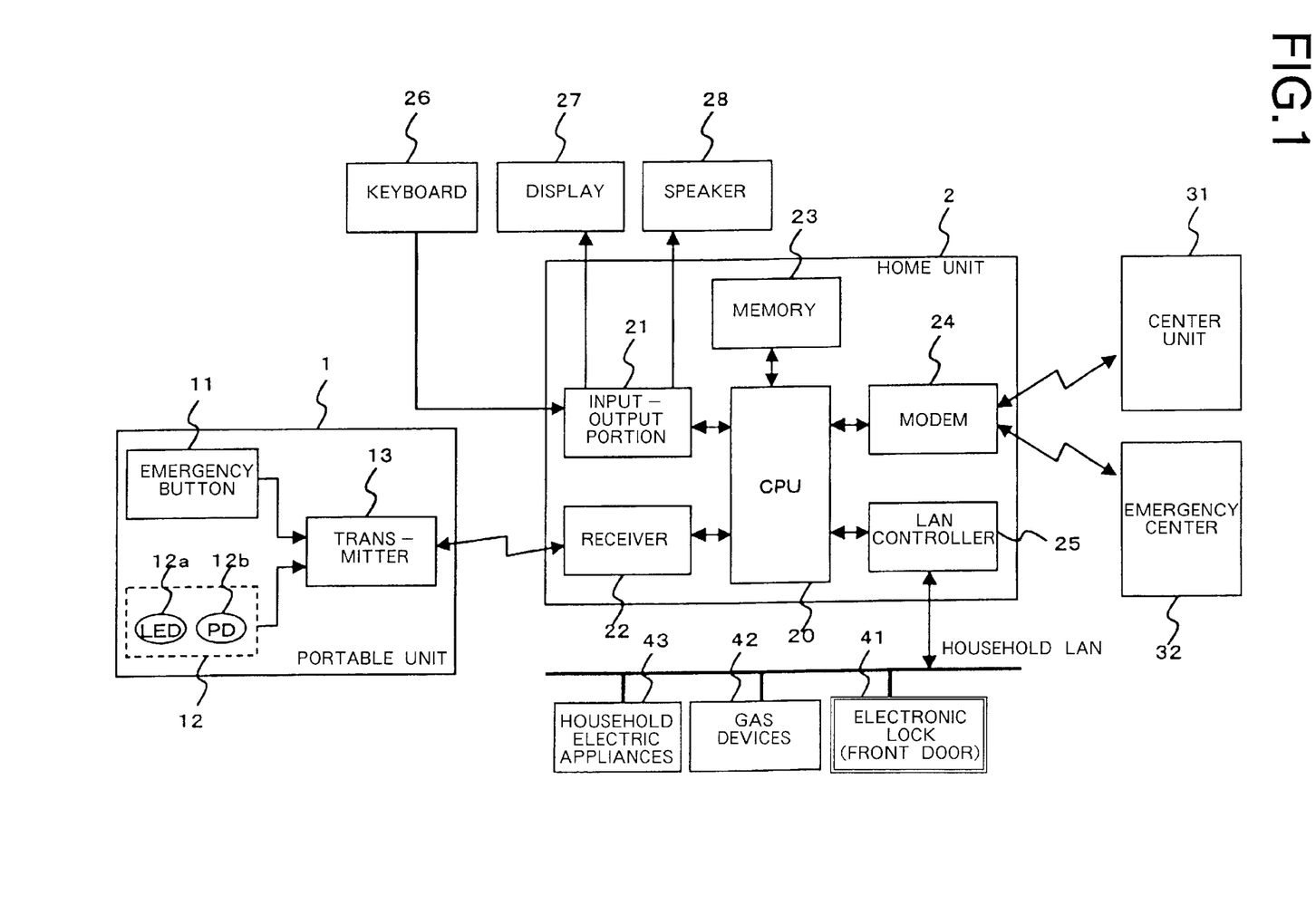
FIG. 1 is a block diagram showing the overall construction of a home medical management system embodying the invention.

With reference to FIG. 1, the home medical management system of the present.invention comprises a home unit 2 installed at the user's home, a portable unit 1 adapted to wirelessly communicate with the home unit 2, and a center unit 31 connected to the home unit 2 by a telephone line. An emergency center 32 is connected also to the home unit 2 by the telephone line.

The portable unit 1 is of the wrist watch type and is used as worn on the wrist of the user. The portable unit 1 comprises an emergency button 11, physiological quantity sensor 12 and transmitter 13. The emergency button 11 is used by the user when he desires to make contact with the emergency center 32 registered for an emergency call, in the event the user is brought into poor physical condition. When pushed, the button feeds an emergency signal to the transmitter 13. The physiological quantity sensor 12, which is adapted to measure a physiological quantity, feeds an output signal to the transmitter 13 at a predetermined interval of time.

A pulse sensor serves as the sensor 12 in this embodiment. The sensor 12 comprises as arranged in contact with the skin of the user an LED 12a for emitting light involving a wavelength range corresponding to the color of red blood cells, and a photodetector 12b for receiving the light upon reflection. The light emitted by the LED 12a and received upon reflection increases in quantity with an increase in the blood flow rate, i.e., the flow rate of red cells, so that variations in the blood flow rate are reflected in the output of the photodetector 12b. Thus, the pulse rate is measured based on variations in the blood flow rate.

When receiving .the output signal of the photodetector 12b of the sensor 12 or the emergency signal from the emergency button 11, the transmitter 13 transmits the signal as combined with a carrier of predetermined frequency.

The home unit 2 has a CPU 20 as the main component and comprises an input-output portion 21, receiver 22, memory 23, modem 24 and LAN controller 25 which are connected to the CPU 20. Connected to the input-output portion 21 is a keyboard 26 which is used by the user for inputting instructions and various items of data to the home unit 2. Also connected to the input-output portion 21 is a display 27 for use in displaying the instructions and data entered by the keyboard 26 and displaying video images input via the telephone line. A speaker 28 is further connected to the input-output portion 21 for use in outputting a sound or voice input through the telephone line.

The receiver 21 of the home unit 2 receives the radio waves sent from the portable unit 1, and the signal multiplexed in the waves is fed to the CPU 20, which in turn detects pulse waves from the input signal and calculates the pulse rate per minute from the peak-to-peak interval of the pulse waves. The calculated pulse rate is compared with a reference value for the judgment of the physical condition of the user, and control signals are fed to devices based on the result. Serving as the reference value is the average pulse rate of the user when he is at rest, the average being determined in advance and stored in the memory 23. Consequently, the physical condition of the user can be judged free of the influence of person-to-person differences in pulse rate to ensure reliable judgment.

The modem 24 is connected to the public telephone network. In the event of an emergency, the pre-registered telephone number of the emergency center 32 is automatically dialed to conduct communication with the emergency center 32.

The LAN controller 25 is connected to various devices such as household electric appliances 43, gas devices 42, electronic lock 41 on the front door, etc. by way of household LAN. These devices are controlled in accordance with control signals from the CPU 20.

Figure 2:
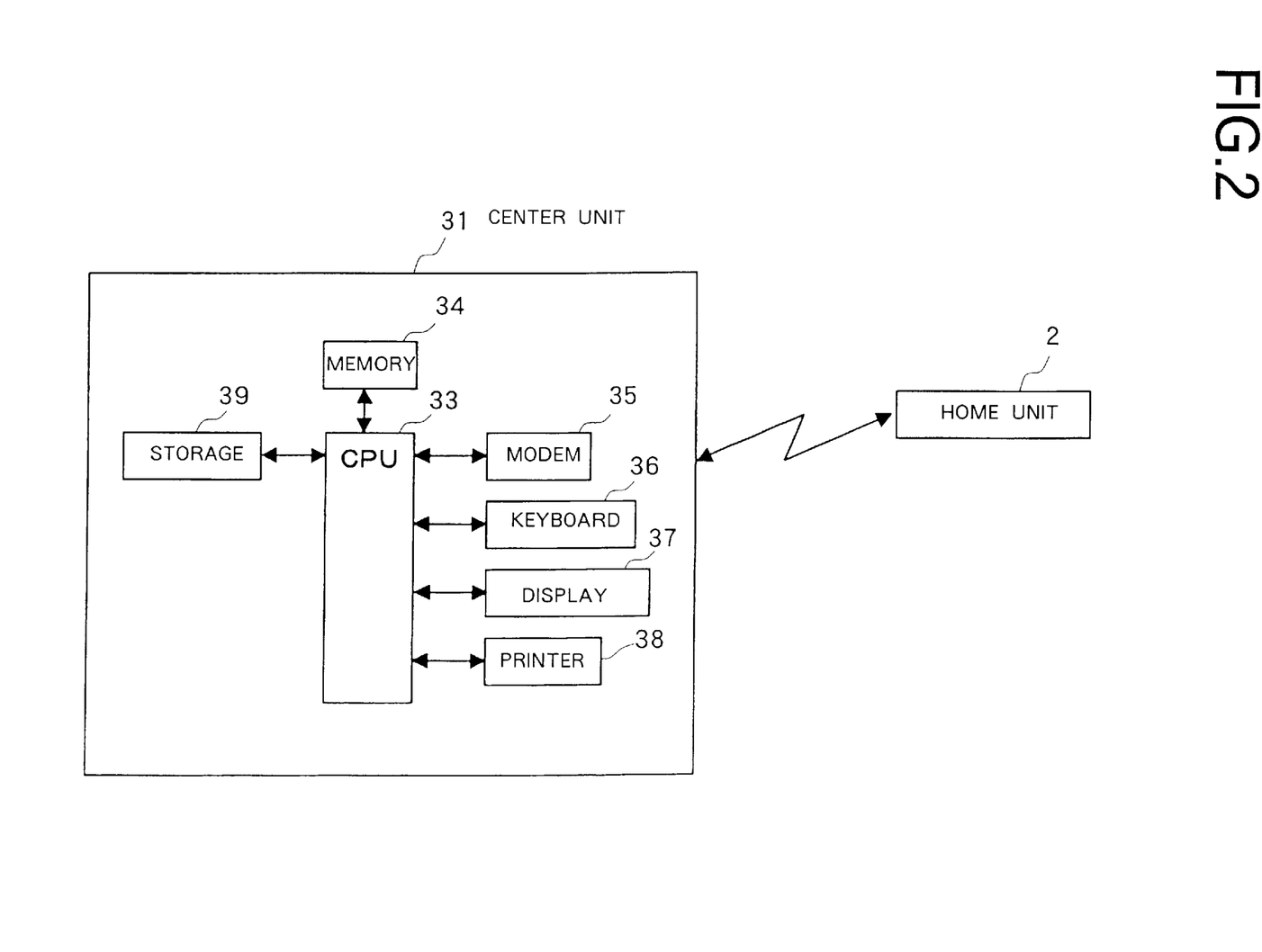
FIG. 2 is a block diagram showing the construction of a center unit in the system.

On the other hand, the center unit 31 has a CPU 33 as its main component and comprises a memory 34, modem 35, keyboard 36, display 37, printer 38 and storage 39 which are connected to the CPU 33 as shown in FIG. 2. The keyboard 36 is used by the attendant for entering instructions and various items of data into the center unit 31. The modem 35 is connected to the public telephone network for allowing communication with the home unit 2. The display 37 is used for displaying the instructions and data input by the keyboard 36. The printer 38 is used for outputting the data transmitted from the home unit 2. The memory 34 is used for the calculation by the CPU 33, while the storage 39 has stored therein data such as the telephone numbers, addresses, anamneses of the users. Further registered in the storage according to the third embodiment to be described later are passwords for unfastening the electronic locks on front doors.

The printer 38 of the center unit 31 is installed in the command room of the emergency center 32 or waiting room thereof for attendants.

First Embodiment

Figure 3:
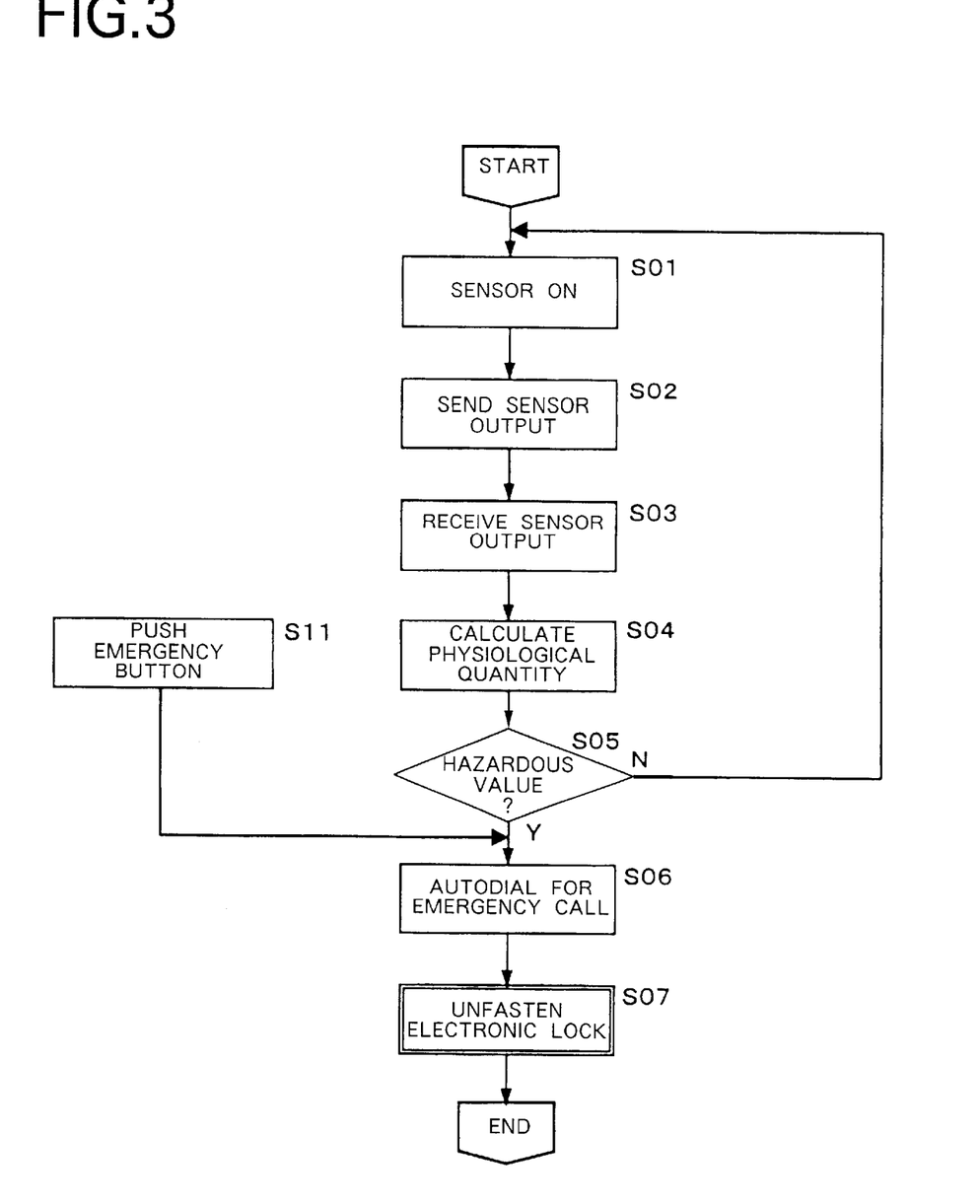
FIG. 3 is a flow chart for illustrating the operation of controlling an electronic lock according to a first embodiment of home medical management system.

FIG. 3 shows the control operation of a first embodiment in the home medical management system having the foregoing construction. When the portable unit 1 of the wrist watch type is worn by the user on his wrist, the measurement of the pulse rate is started first (step SO1). At this time, the LED 12a and photodetector 12b of the portable unit 1 are held generally in intimate contact with the wrist of the user, the wrist is irradiated with the light emitted by the LED 12a, and the light is received by the photodetector 12b upon reflection.

The light impinging on the photodetector 12b is photoelectrically converted into an electric sensor output signal, which is then fed to the transmitter 13. The sensor output signal is multiplexed into a carrier of predetermined frequency by the transmitter 13 and then sent to the home unit 2 (step SO2).

The multiple signal transmitted from the transmitter 13 is received by the receiver 22 of the home unit 2, and the sensor output signal is extracted and fed to the CPU 20 (step SO3). The CPU 20 detect's pulse waves from the output signal and calculates the peak-to-peak interval of the waves. The pulse rate per minute is calculated as a physiological quantity from the average value of peak intervals during the latest 10-sec period (step SO4).

The pulse waves and pulse rate thus obtained are presented on the display 27. The pulse rate is compared with a reference value, and if the difference is not smaller than a threshold value (e.g., 40), the rate is interpreted as being a hazardous value (step SO5).

If the pulse rate is judged to be hazardous, the presentation on the display 27 goes on and off, an alarm sound is produced from the speaker 28, and the CPU 20 further feeds to the modem 24 an autodialing control signal for the emergency center 32. In response to the control signal, the modem 24 places a call to the emergency center 32 which has been registered for an emergency call (step SO6). In this communication, voice data as to the user's address which is stored in the memory 23 in advance is sent first. On receiving the emergency call, the emergency center 32 makes arrangements to send an ambulance to the user's home.

When the pulse rate is judged to be hazardous, CPU 20 further feeds an emergency control signal to the LAN controller 25, which in turn feeds an unlocking control signal to the electronic lock 41 on the front door via the household LAN (step SO7). As a result, the electronic lock is automatically unfastened.

Further even if the pulse rate is not hazardous as when the user suffers an injury, steps SO6 and SO7 are executed to meet the emergency if the user pushes the emergency button 11 on the portable unit 1 (step S11).

Upon the arrival of the ambulance at the user's home, the attendants enter the room where the user is present through the front door as unlocked to rescue and transport the user.

Thus, the present embodiment is so adapted as to unfasten the electronic lock 41 on the front door in operative relation with communication with the emergency center 32, so that the attendants of the ambulance arriving at the user's home can enter the interior through the unlocked front door to rescue and transport the user promptly.

Further if the pulse rate is judged to be hazardous, the presentation on the display 27 goes on and off, with an alarm sound produced from the speaker 28 according to the present embodiment. This enables the user to immediately recognize that the pulse rate is hazardous to deal with the emergency.

Although an emergency is reported to the user using the display 27 and the speaker 28 which are connected to the center unit 2 according to the present embodiment, the center unit 2 may send a control signal to the portable unit 1 wirelessly, for example, to vibrate the portable unit 1 and to thereby notify the user of the emergency.

Further even in the case where a report is made by the display 27, speaker 28 or portable unit 1, the electronic lock 41 on the front door may be so adapted as to be fastened, for example, by pushing the emergency button 11 twice in succession after the user recovers his health by medication or taking a rest. The user then need not go to the location of the front door and fasten the unfastened lock 41 again, hence convenience.

Although the emergency center 32 is registered as the destination of the emergency call according to the present embodiment, the center unit 31 may also serve as a destination of emergency calls so as to notify the center unit 31 of the occurrence of an emergency. Since the center unit 31 has stored therein medical data such as the anamneses of the users, more appropriate medical care can then be provided.

In the case where a PHS (personal handy-phone system) terminal is used as the transmitter 13 of the portable unit of the present embodiment, the user can be located based on the position detecting function of the PHS terminal. Accordingly, the embodiment is made serviceable also for the places, other than the user's home, where electronic locks for use with the present system are provided for unfastening the desired lock only in accordance with the position of the user. This increases the range over which the user can behave with safety.

According to the present embodiment, the pulse rate is judged to be hazardous if different from the reference value by at least 40, whereas the pulse rate may be interpreted as indicating an emergency when outside a reference range, for example, when up to 40 or at least 200.

Although the pulse rate is used as the physiological quantity to be measured by the sensor 12, it is possible to use various known physiological quantities such as blood pressure, electrocardiogram wave patterns, body temperatures, etc.

Further although the physiological quantity data is compared with a single reference value for the judgment of occurrence of an emergency, a plurality of reference values an be used for the determination of the degree of hazard of the emergency so as to notify the emergency center of the emergency and automatically unfasten the front door electronic lock in the event of a high degree of hazard, while if the degree of hazard is low, the procedure taken is limited only to the reporting the emergency to the center, with the front door of the user held locked for the user to unlock the door after the arrival of the ambulance.

Second Embodiment

The second embodiment is so designed that in the event of an emergency developing, the home unit 2 notifies the emergency center 32 of the emergency and transmits a password for opening an electronic lock on the front door of the user's home to the center unit 31, enabling the ambulance attendant to unfasten the lock using the password received by the center unit 31.

Figure 4:
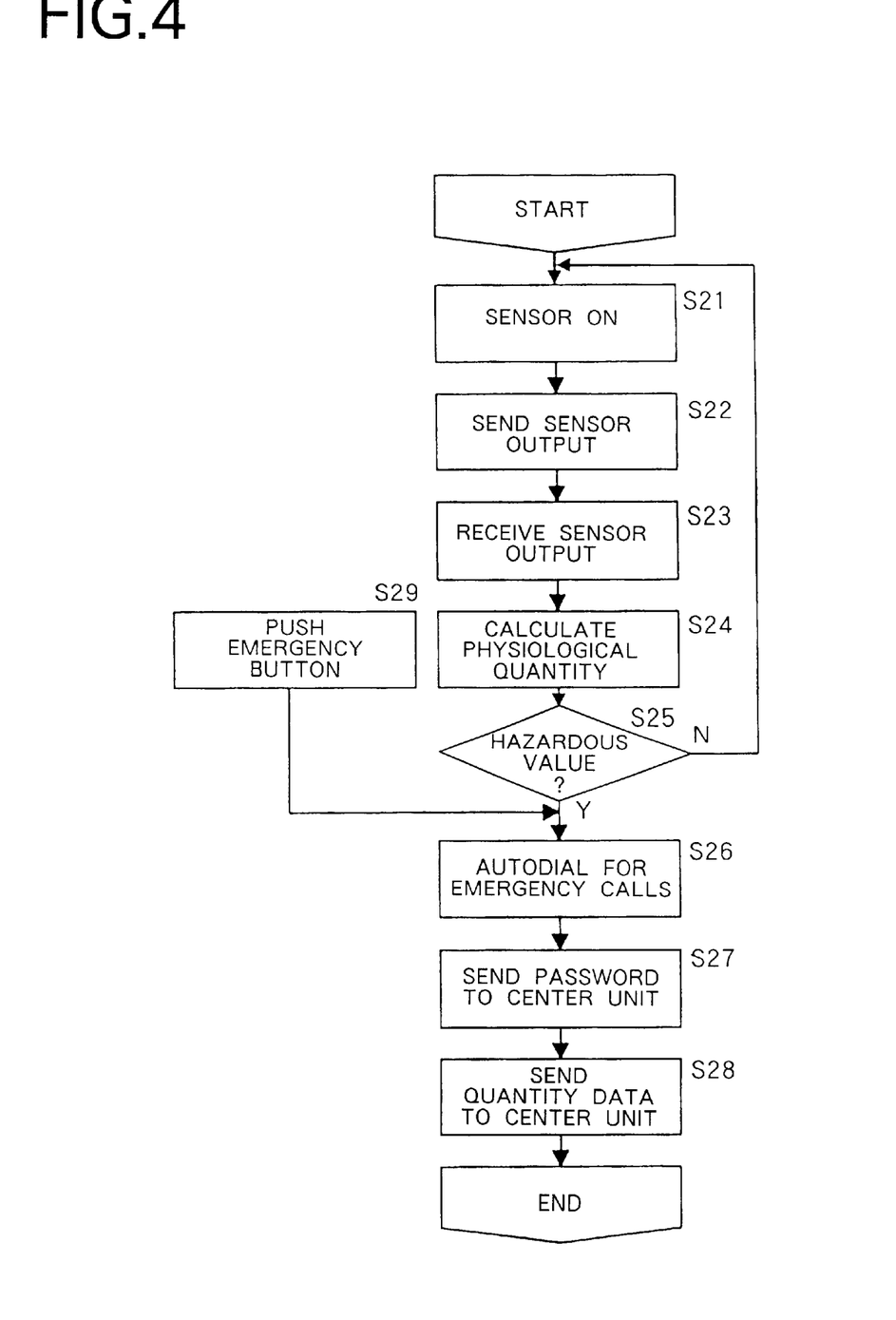
FIG. 4 is a flow chart for illustrating the control operation of a home unit according to a second embodiment of home medical management system.

FIG. 4 shows the control operation of the home unit 2 according to the second embodiment. When the user wears the portable unit 1 of the wrist watch type on his wrist, measurement is started first (step S21), and an output signal is sent from the sensor to the home unit 2 (step S22).

When the sensor output signal is received by the home unit 2 (step S23), the peak interval of pulse waves is calculated from the output signal, and the pulse rate per minute is calculated based on the result (step S24). The pulse rate obtained is compared with a reference value. The rate is judged to be a hazardous value if the difference is not smaller than a threshold value (step S25).

If the pulse rate is found hazardous, the emergency center and the center unit already registered for emergency calls are dialed (step S26).

The emergency center is notified of the development of an emergency, and the password for unfastening the electronic lock and the physiological quantity are sent to the center unit (steps S27, S28).

Further even if the pulse rate is not hazardous, an emergency handling procedure is performed if the user pushes the emergency button 11 on the portable unit 1 (step S29).

Figure 5:
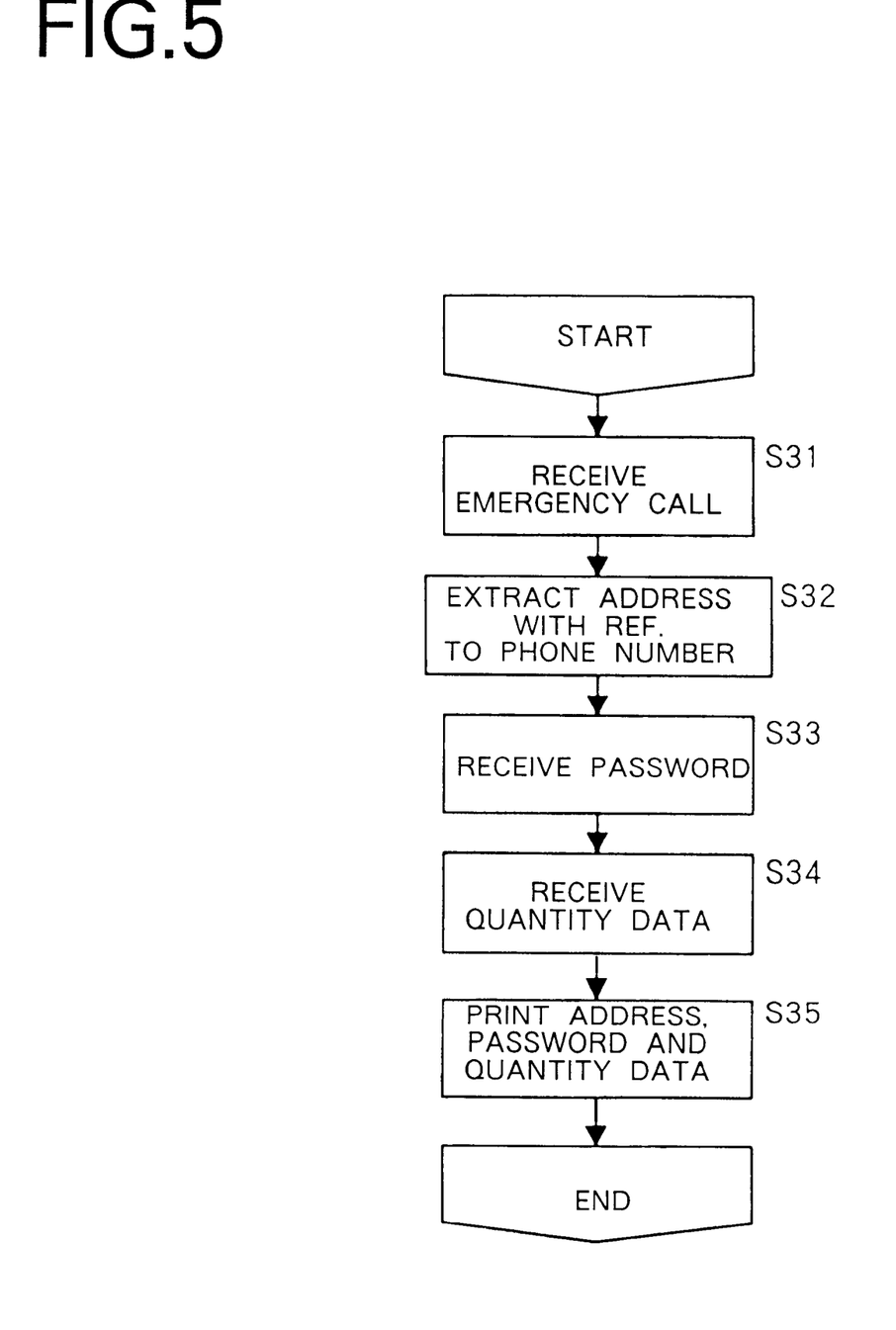
FIG. 5 is a flow chart for illustrating the control operation of the center unit according to the second embodiment.

With reference to FIG. 5, on the other hand, the center unit 31 receives an emergency call from the home unit (step S31). At this time, the receiver is notified of the telephone number of the transmitter utilizing the caller telephone number reporting service provided by the telephone service company. Accordingly, with reference to the telephone number of the user (transmitter), the address of the user is extracted from the data registered in the storage 39 (step S32). The password and the physiological quantity data sent from the home unit are also received by the center unit (steps S33, S34). The extracted address of the user, and the password and quantity data received are printed on scratch paper by the printer 38.

The printed paper is handed to the ambulance attendant, who drives the ambulance toward the user's home at the address on the print. Upon arriving at the user's home, the attendant inputs the printed password to the electronic lock on the front door, whereby the lock is unfastened. The attendants then enter the user's home to rescue and transport the user. Emergency treatment is given to the user with reference to the printed data as to the physiological quantity.

Thus, the present embodiment is adapted to send the password for opening the electronic lock of the user's home to the center unit for the ambulance attendant to open the electronic lock with the password. Accordingly, the front door is held locked until the ambulance attendants arrive at the user's home. This assures the user's home of security.

Third Embodiment

When an emergency call is placed to the home unit 2 from the center unit 3 in the event of an emergency occurring, the corresponding password registered in the center unit 3 in advance is output for the ambulance attendant to open the electronic lock on the front door of the user's home according to the third embodiment.

Figure 6:
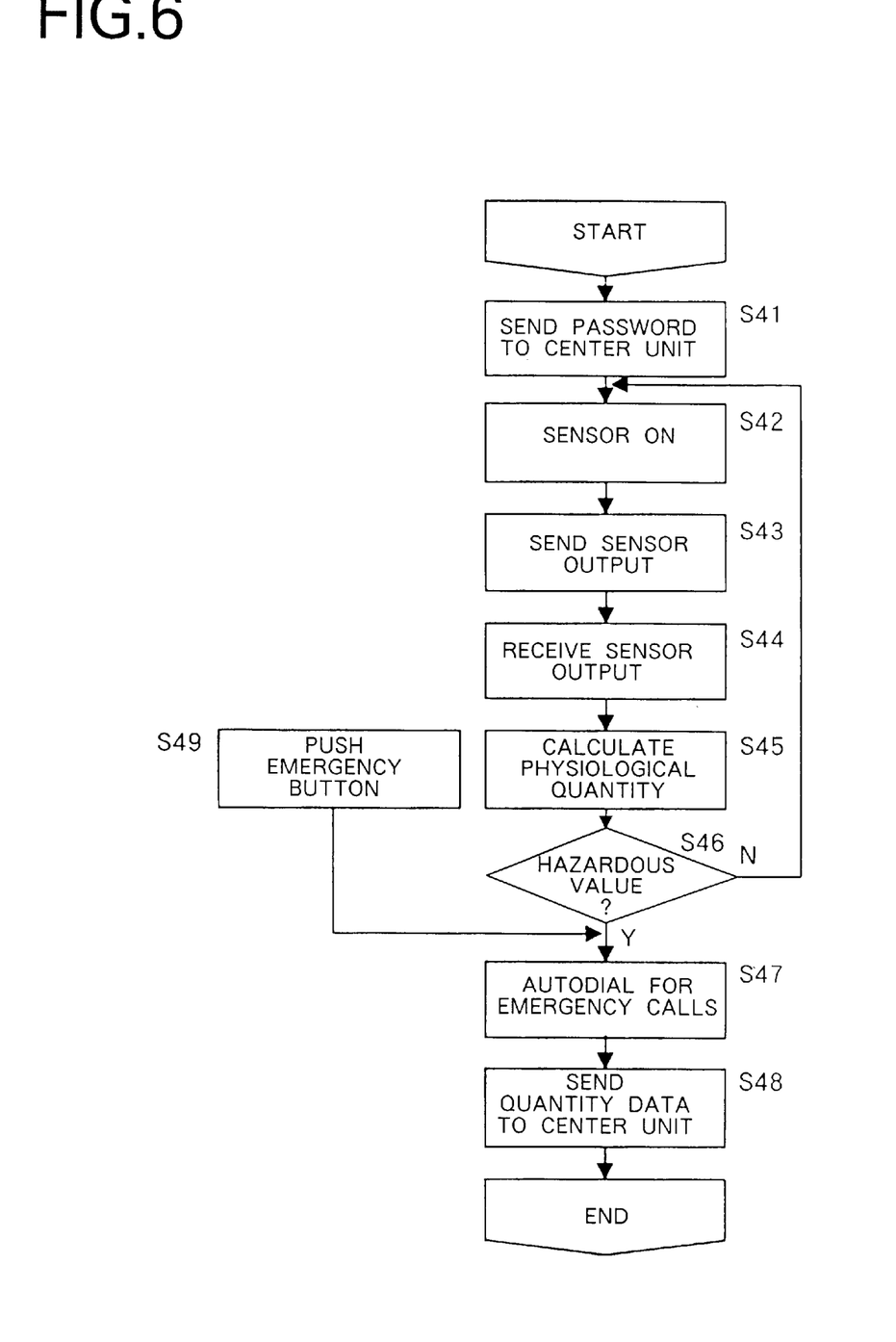
FIG. 6 is a flow chart for illustrating the control operation of he home unit according to a third embodiment of home medical management system.

FIG. 6 shows the control operation of the home unit 2. The password for opening the user's home electronic lock is sent in advance from the home unit 2 to the center unit 3 (step S41). When the user thereafter wears the portable unit 1 on his wrist, measurement is started (step S42), and a sensor output signal is sent to the home unit 2 (step S43).

The home unit 2 receives the sensor output signal (step S44), whereupon the peak interval of pulse waves is calculated from the signal, and the pulse rate per minute is calculated from the result (step S45). The pulse rate obtained is compared with a reference value and interpreted as being a hazardous value if the difference it not smaller than a threshold value (step S46).

If the pulse rate is found to be hazardous, the emergency center and the center unit which are specified in advance for placing an emergency call to are dialed (step S47). The emergency center is notified of the emergency, and the physiological quantity data is sent to the center unit (step S48).

Further even if the pulse rate is not hazardous, an emergency handling procedure is performed if the user pushes the emergency button 11 on the portable unit 1 (step S49).

Figure 7:
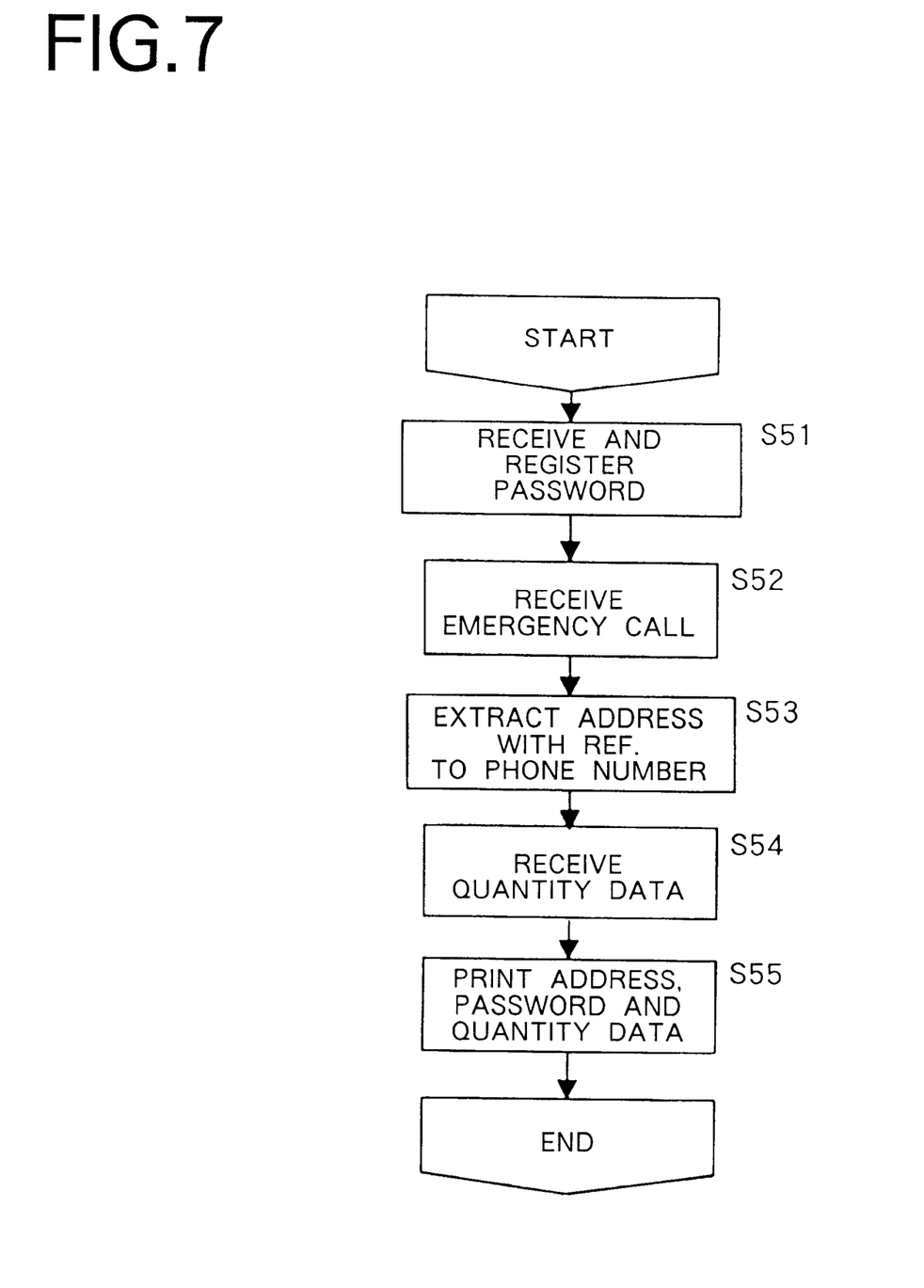
FIG. 7 is a flow chart for illustrating the control operation of the center unit according to the third embodiment.

With reference to FIG. 7, on the other hand, the center unit 31 receives from the home unit the password, which is registered in advance (step S51). When an emergency call is thereafter received (step S52), the address of the transmitter of the emergency call (user) is extracted with reference to his telephone number (step S53). Further received is the physiological quantity data sent from the home unit (step S54).

Subsequently, the password registered in advance is extracted with reference to the telephone number of the user placing the emergency call, and the password is printed by the printer on scratch paper along with the address of the user extracted and the physiological quantity data received (step S55).

The printed paper is handed to the ambulance attendant, who drives the ambulance toward the user's home at the address on the print. Upon arriving at the user's home, the attendant inputs the printed password to the electronic lock on the front door, whereby the lock is unfastened for the attendants to rescue and transport the user.

Thus according to the present embodiment, the password for opening the electronic lock of the user's home is registered in advance in the center unit for the ambulance attendant to open the electronic lock of the user with the extracted password. Accordingly, the lock is held fastened until the ambulance attendants arrive at the user's home. This assures the user's home of security.

What is claimed is:

1. An electronic lock control system for controlling fastening and unfastening of an electronic lock attached to a door, the system being characterized in that the system comprises means to be worn on the body of the user for measuring a physiological quantity, and means for conducting communication with a predetermined destination and transmitting an unfastening command to the electronic lock, in accordance with the result of measurement by the physiological quantity measuring means.

2. An electronic lock control system according to claim 1 which comprises means for notifying the user that the unfastening command has been transmitted from the transmitting means to the electronic lock.

3. An electronic lock control system according to claim 2 which comprises means for canceling the notification by the notifying means, and the transmitting means transmits the unfastening command to the electronic lock in operative relation with the cancellation of the notification by the canceling means.

4. A home medical management system comprising a portable unit (1) to be worn on the body of the user for measuring a physiological quantity, and a home unit (2) installed at a home of the user and adapted to wirelessly communicate with the portable unit (1) for judging the physical condition of the user according to the physiological quantity measured by the portable unit (1) and notifying a predetermined destination of occurrence of an emergency in the event of the emergency occurring, the system being characterized in that the home unit (2) is provided with means for transmitting an unfastening command to an electronic lock fastening a door of the user's home in the event of an emergency occurring.

5. A home medical management system according to claim 4 wherein an emergency center (32) for dispatching ambulance attendants is registered as the destination to be notified of the occurrence of the emergency.

6. A home medical management system comprising a portable unit (1) to be,worn on the body of the user for measuring a physiological quantity, and a home unit (2) installed at a home of the user and adapted to wirelessly communicate with the portable unit (1) for judging the physical condition of the user according to the physiological quantity measured by the portable unit (1) and notifying a predetermined destination of occurrence of an emergency in the event of the emergency occurring, the system being characterized in that the home unit (2) is provided with means for transmitting to the destination a password for unfastening an electronic lock fastening a door of the user's home in the event of an emergency occurring.

7. A home medical management system comprising a portable unit (1) to be worn on the body of the user for measuring a physiological quantity, and a home unit (2) installed at a home of the user and adapted to wirelessly communicate with the portable unit (1) for judging the physical condition of the user according to the physiological quantity measured by the portable unit (1) and notifying an emergency center (32) for dispatching ambulance attendants of occurrence of an emergency in the event of the emergency occurring, the system being characterized in that the system comprises a center unit (31) connected to home units (2) of respective users and adapted for communication therewith, each of the home units (2) having means for notifying the center unit (1) of occurrence of an emergency, the center unit (31) comprising means having stored therein a password for unfastening an electronic lock attached to a door of the home of each of the users, means for extracting the password for unlocking the door of the home of the user developing an emergency in response to the notification of occurrence of the emergency from his;home unit (2), and means for outputting the extracted password.

8. A home medical management system according to claim 7 wherein the center unit (31) has registered therein the password for unlocking the door of the home of each user and his home address, and the center unit (31) extracts and outputs the password for unlocking the door of the home of the user developing an emergency and the home address of the same user, in response to the notification of occurrence of the emergency from his home unit (2).

9. A home medical management system according to claim 7 wherein the outputting means of the center unit (31) is installed at a location where the attendant of the emergency center (32) can receive the output thereof.

* * * * *